US012787958B2

(12) United States Patent
Shrestha

(10) Patent No.: US 12,787,958 B2
(45) Date of Patent: Nov. 10, 2026

(54) ARUGULA VARIETY 'CN SROC 2520'

(71) Applicant: CN SEEDS LTD, Ely (GB)

(72) Inventor: Sujit Hari Tha Shrestha, Ely (GB)

(73) Assignee: CN SEEDS LTD, Ely (GB)

( * ) Notice: Subject to any disclaimer, the term of this patent is extended or adjusted under 35 U.S.C. 154(b) by 231 days.

(21) Appl. No.: 18/594,768

(22) Filed: Mar. 4, 2024

(65) Prior Publication Data

US 2025/0275512 A1 Sep. 4, 2025

(51) Int. Cl.

*A01H 5/12* (2018.01)
*A01H 6/20* (2018.01)
*C12Q 1/6895* (2018.01)

(52) U.S. Cl.

CPC ............... *A01H 6/205* (2018.05); *A01H 5/12* (2013.01); *C12Q 1/6895* (2013.01); *C12Q 2600/156* (2013.01)

(58) Field of Classification Search

None

See application file for complete search history.

(56) References Cited

U.S. PATENT DOCUMENTS 12,137,652 B2 * 11/2024 Langeraar ................ A01H 6/14

OTHER PUBLICATIONS

Ex parte C, 27 U.S.P.Q.2d 1492 (Bd.Pat.App.&Interf.), 1992 WL 515817,Board of Patent Appeals and Interferences (Year: 1992) (Year: 1992).*

Haun et al, The Composition and Origins of Genomic Variation among Individuals of the Soybean Reference Cultivar Williams 82, Plant Physiology, Feb. 2011, vol. 155, pp. 645-655 (Year:2011) (Year: 2011).*

Grobkinsky, Plant phenomics and the need for physiological phenotyping across scales to narrow the genotype-to-phenotype knowledge gap, Journal of Experimental Botany, vol. 66, No. 18, pp. 5429-5440, 2015 (Year: 2015).*

UPOV,Explanatory Notes on Essentially Derived Varieties Under the 1991 Act of the UPOV Convention (Year:2017) (Year: 2017).*

Mcgowan, Appeal 2019-006060, U.S. Appl. No. 14/996,093 (Year:2020) (Year: 2020).*

USDA, Applying for a Plant Variety Certificate of Protection, www.ams.usda.gov (Year:2023) (Year: 2023).*

Banjac et al., "In Vitro Shoot Multiplication and Regeneration of the Recalcitrant Rocket (*Eruca sativa* Mill.) Variety Domaca Rukola," Horticulturae, vol. 9, No. 533, pp. 1-18 (2023).

Plant Variety Protection Certificate No. 202300095 for Arula 'Revolution', also referred to as 'CN SROC 2520'.

Variety Data Sheet of European Union (QZ) Plant Breeders' Rights Grant No. 62972 for breeder's reference 'cn sroc 2520', denomination Revolution, rejected or withdrawn denomination Boudha.

Variety Data Sheet of United Kingdom (GB) Plant Breeders' Rights Grant No. 35548 for breeder's reference 'CN SROC 2520', proposed denomination Revolution.

Variety Data Sheet of Australia (AU) Plant Breeders' Rights Application No. 2022198 for breeder's reference 'CN SROC 2520', denomination Revolution.

* cited by examiner

*Primary Examiner* — Amjad Abraham
*Assistant Examiner* — Christina L Meadows
(74) *Attorney, Agent, or Firm* — Panitch Schwarze Belisario & Nadel LLP

(57) ABSTRACT

An arugula cultivar, designated 'CN SROC 2520' is disclosed. The invention relates to seeds of 'CN SROC 2520', plants and plant parts of 'CN SROC 2520', methods of producing an arugula plant by breeding with 'CN SROC 2520', arugula plants or plant parts derived from 'CN SROC 2520', including 'CN SROC 2520'-derived seed(s) and plant(s) obtained through breeding or by introducing a transgene or mutation.

21 Claims, 2 Drawing Sheets

ARUGULA VARIETY 'CN SROC 2520'

FIELD OF THE INVENTION

The present invention relates to the field of plant breeding. In particular, this invention relates to new arugula, *Eruca sativa* Mill., variety designated 'CN SROC 2520', also known as REVOLUTION®.

BACKGROUND OF THE INVENTION

Cultivated forms of arugula belong to the species *Eruca sativa* Mill. that is grown for its edible leaves. It is also known as salad rocket, garden rocket, wild rocket, rucola, and roquette. As a crop, arugula is grown commercially wherever environmental conditions permit the production of an economically viable yield. Arugula is consumed primarily as fresh, raw product and occasionally as a cooked vegetable.

*Eruca sativa* Mill. is of the Brassicaceae family. Arugula is related to cabbage, kale, cauliflower, and broccoli and is an annual plant. Arugula is an increasingly popular crop. As a result of this demand, there is a continued need for new arugula varieties. In particular, there is a need for improved arugula varieties.

BRIEF SUMMARY OF THE INVENTION

In order to meet these needs, the present invention is directed to improved arugula varieties. In particular, the present invention provides methods and compositions related to a new arugula variety, designated 'CN SROC 2520', which has a combination of traits including dark green colored leaves, with a small first true leaf that has a presence of hint of lobes, narrow to medium width of primary lobes, strong to very strong secondary lobing, an angle of primary lobing which is almost horizontal with round/smooth end, and has medium to late bolting/flowering.

In one embodiment, the present invention is directed to arugula, *Eruca sativa* Mill., seed(s) designated as 'CN SROC 2520', wherein a representative sample of the seed having been deposited under NCIMB Accession Number NCIMB 44773. In one embodiment, the present invention is directed to a *Eruca sativa* Mill. arugula plant and parts isolated therefrom produced by growing 'CN SROC 2520' arugula seed. In another embodiment, the present invention is directed to a *Eruca sativa* Mill. plant and parts isolated therefrom having all the physiological and morphological characteristics of a *Eruca sativa* Mill. plant produced by growing 'CN SROC 2520' arugula seed.

Arugula plant parts include arugula leaves, parts of arugula leaves, shoots, stems, microspore, pollen, ovary, ovules, flowers, a cutting, a root, a stem, a cell, a protoplast and the like. In another embodiment, the present invention is further directed to arugula leaves, parts of arugula leaves, shoots, stems, microspore, pollen, ovary, ovules, flowers, a cutting, a root, a stem, a cell, a protoplast and the like isolated from 'CN SROC 2520' arugula plants.

In another embodiment, the present invention is further directed to tissue culture of regenerable cells or protoplasts from 'CN SROC 2520' arugula plants or plant parts thereof, and to arugula plants regenerated from the tissue culture, where the plant has all of the morphological and physiological characteristics of 'CN SROC 2520' arugula plants. In certain embodiments, the regenerable cells or protoplasts of the tissue culture are derived from a leaf, pollen, an embryo, a cotyledon, a hypocotyl, a meristematic cell, a root, a root tip, an anther, a flower, a seed, a stem, or the like.

In another embodiment, the present invention is directed to vegetatively propagating an 'CN SROC 2520' plant by collecting tissue capable of being propagated from an 'CN SROC 2520' plant and producing a rooted plant from the collected tissue.

In still another embodiment, the present invention is directed to an F1 hybrid *Eruca sativa* Mill. arugula seed, plants grown from the seed, and a plant part, such as a leaf, isolated therefrom having 'CN SROC 2520' as a parent, where 'CN SROC 2520' is grown from 'CN SROC 2520' arugula seed having NCIMB Accession Number NCMB 44773. In other embodiments, the present invention is directed to a method of making arugula seeds by crossing a male parent arugula plant with a female parent arugula plant and harvesting the resultant arugula seeds therefrom, wherein said male parent arugula plant and/or said female parent arugula plant is the 'CN SROC 2520' variety. Further embodiments are F1 arugula seed(s) produced by such method and F1 arugula plant(s) produced by growing the F1 arugula seeds.

In another embodiment, the present invention is directed to producing a seed of a 'CN SROC 2502'-derived arugula plant by crossing a plant of 'CN SROC 2520' with a second arugula plant and then a seed of a 'CN SROC 2520'-derived arugula plant forms. Further embodiments, include crossing the plant grown from the 'CN SROC 2520'-derived seed with itself, with a second arugula plant, or with 'CN SROC 2520' to yield additional 'CN SROC 2520'-derived arugula seed(s) and growing these additional 'CN SROC 2520'-derived arugula seed(s) to yield additional 'CN SROC 2520'-derived arugula plants, optionally the crossing and growing steps is repeated, such as for an additional 3-10 generations, to generate further 'CN SROC 2520'-derived arugula plants.

In another embodiment, the present invention is further directed to a method of breeding arugula plants by crossing an arugula plant with a plant grown from 'CN SROC 2520' arugula seed having NCIMB Accession Number NCIMB 44773. In still another embodiment, the present invention is further directed to arugula plants, arugula parts from the arugula plants, and seeds produced therefrom where the arugula plant is isolated by the breeding method of the invention.

In another embodiment, the present invention is directed to methods of producing an herbicide resistant arugula plant by introducing a gene conferring herbicide resistance into an arugula plant produced by growing 'CN SROC 2520' arugula seed. Certain embodiments are also directed to herbicide resistant arugula plants produced by such methods.

In another embodiment, the present invention is directed to methods of producing a pest or insect resistant arugula plan by introducing a gene conferring pest or insect resistance into an arugula plant produced by growing 'CN SROC 2520' arugula seed, and to pest or insect resistant arugula plants produced by such methods.

In another embodiment, the present invention is directed to methods of producing a disease resistant arugula plant by introducing a gene conferring disease resistance into an arugula plant produced by growing 'CN SROC 2520' arugula seed, and to disease resistant arugula plants produced by such methods.

In another embodiment, the present invention is directed to methods of introducing at least one new trait into a plant of arugula variety 'CN SROC 2520', by breeding a 'CN SROC 2520' plant with a second variety and backcrossing or by introducing a mutation or transgene conferring the at least one new trait into a 'CN SROC 2520' plant. Certain embodiments are also directed to arugula plants having a value-added trait produced by such methods. In certain embodiments, the at least one new trait includes a value-added trait.

In certain embodiment, the present invention is directed to methods of introducing a desired trait into arugula variety 'CN SROC 2520', by: (a) crossing a 'CN SROC 2520' plant, where a sample of 'CN SROC 2520' arugula seed was deposited under NCIMB Accession Number NCIMB 44773, with a plant of another arugula variety that contains a desired trait to produce progeny plants, such desired trait include male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'CN SROC 2520' plant to produce backcross progeny plants; (d) selecting for backcross progeny plants that have the desired trait and essentially all of the physiological and morphological characteristics of arugula variety 'CN SROC 2520'; and (e) repeating steps (c) and (d) two or more times in succession to produce selected third or higher backcross progeny plants that comprise the desired trait. Certain embodiments are also directed to arugula plants produced by such methods, where the plants have the desired trait and essentially all of the physiological and morphological characteristics of arugula variety 'CN SROC 2520'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

In another embodiment, the present invention provides for single gene converted plants of 'CN SROC 2520'. The single transferred gene may be a dominant or a recessive allele. For example, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage.

In another embodiment, the present invention relates to methods for determining the genotype of a plant of arugula variety 'CN SROC 2520' or a first generation progeny thereof by obtaining a sample of nucleic acid from the plant and comparing to a sample of nucleic acids obtained from a known reference plant, detecting a plurality of polymorphisms between the two nucleic acid samples.

In a further embodiment, the present invention relates to methods for developing arugula plants in an arugula plant breeding program using 'CN SROC 2520' and plant breeding techniques including recurrent selection, backcrossing, pedigree breeding, restriction fragment length polymorphism enhanced selection, and genetic marker enhanced selection. Seeds, arugula plants, and parts thereof, produced by such breeding methods are also part of the invention.

The invention even further relates to a method of producing arugula which may comprise: (a) cultivating to the vegetative plant stage a plant of arugula variety 'CN SROC 2520', representative seed of which having been deposited under NCIMB Accession Number NCIMB 44773, and (b) harvesting arugula leaves from the plant. The invention further comprehends packaging and/or processing the arugula plants, or leaves therefrom.

In still another embodiment, the present invention is further directed to packaging material containing 'CN SROC 2520' plant parts. Such packaging material includes but is not limited to boxes, plastic bags, etc. The 'CN SROC 2520' plant parts may be combined with other plant parts of other plant varieties.

In addition to the exemplary aspects and embodiments described above, further aspects and embodiments will become apparent by reference by study of the following description.

Deposit

The Deposit will be made under NCIMB Accession Number NCIMB 44773 pursuant to the terms of the Budapest Treaty. Upon issuance of a patent, all restrictions upon the deposit will be remove, and the deposit is intended to meet the requirements of 37 C.F.R. §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

Figure 1:
FIG. 1 shows of leaves of new variety 'CN SROC 2520'.
Figure 2:
FIG. 2 shows a photograph of a canopy of new variety 'CN SROC 2520'.

The invention provides methods and compositions relating to plants, seeds and derivatives of a new arugula variety herein referred to as 'CN SROC 2520'. Arugula variety 'CN SROC 2520' is a uniform and stable line, distinct from other such lines.

There are numerous steps in the development of novel, desirable arugula germplasm. Plant breeding begins with the analysis of problems and weaknesses of current arugula germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased leaf size and weight, higher seed yield, improved color, resistance to diseases and insects, tolerance to drought and heat, and better agronomic quality. In some embodiments, the trait is resistance to downy mildew, *Hyaloperonospora parasitica*, also known as *Peronospora parasitica.*

Choice of breeding or selection methods can depend on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least two years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of arugula plant breeding is to develop new, unique, and genetically superior arugula varieties. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial arugula varieties thus requires the development of parental arugula varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population. Then, beginning in the F3, the best individuals in the best families are selected. A family refers to lines that were derived from plants selected from the same progeny from the preceding generation. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different $F_2$ individuals. The number of plants in a population declines with each generation due to failure of some seeds to germinate or some plants to produce at least one seed. As a result, not all of the F2 plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs), which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into arugula varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding are known to those skilled in the art, such as in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., Theor. Appl. Genet., 77:889-892 (1989).

Additional examples of breeding methods are well known in the art and may be applied to breeding with 'CN SROC 2520' variety.

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid F1 with one of the parental genotype of the F1 hybrid.

Bolting. The time it requires for 50% of the plants to begin to have a central flowering stem appear. Bolting is determined by comparison to standard varieties.

Cotyledon. One of the first leaves of the embryo of a seed plant; typically one or more in monocotyledons, two in dicotyledons, and two or more in gymnosperms.

Desired trait(s). As used herein, "desired trait(s)" or "desired characteristic(s)" or "desired attribute(s)" or "desired gene(s)" or "desired phenotype(s)" refers to a phenotypical characteristic or genomic characteristic which is identified in a plant. A desired trait may include a value-added trait and/or a trait that confers herbicide resistance; insect or pest resistance; modified bolting; and resistance to bacterial disease, fungal disease or viral disease.

Essentially all the physiological and morphological characteristics. A plant having essentially all the physiological and morphological characteristics means a plant having the physiological and morphological characteristics of the recurrent parent, except for the characteristics derived from the converted gene(s).

Flower color of petals as used herein is in accordance with the explanation of UPOV TG/245/1 Form, which recognizes three different colors: whitish, cream, and light yellow.

Flower anthocyanin coloration of veins as used herein is in accordance with the explanation of UPOV TG/245/1 Form, which recognizes three different levels: absent or weak, medium, and strong.

Gene. As used herein, "gene" refers to a segment of nucleic acid. A gene can be introduced into a genome of a species, whether from a different species or from the same species, using transformation or various breeding methods.

Leaf anthocyanin coloration of veins: Leaf anthocyanin coloration of veins as used herein is in accordance with the explanation of UPOV TG/245/1 Form, which recognizes either absent or present.

Leaf attitude: Leaf attitude as used herein is in accordance with the explanation of UPOV TG/245/1 Form, which recognizes three different leaf attitudes: erect, semi erect, and horizontal.

Leaf color of blade: Leaf color of blade as used herein is in accordance with the explanation of UPOV TG/245/1 Form, which recognizes two different colors: yellow green and green.

Leaf division. Leaf division as used herein is in accordance with the explanation of UPOV TG/245/1 Form, which recognizes five different levels of leaf division: absent or very weak, weak, medium, strong, and very strong leaf division.

Lear hairiness: Leaf hairiness as used herein is in accordance with the explanation of UPOV TG/245/1 Form, which recognizes three different levels: weak, medium, and strong.

Leaf intensity of color: Leaf intensity of color as used herein is in accordance with the explanation of UPOV TG/245/1 Form, which recognizes three different levels: light, medium, and dark.

Leaf length: Leaf length as used herein is in accordance with the explanation of UPOV TG/245/1 Form, which recognizes three different levels: short, medium, and long.

Leaf secondary lobing: Leaf secondary lobing as used herein is in accordance with the explanation of UPOV TG/245/1 Form, which recognizes five different levels: absent or very weak, weak, medium, strong, and very strong.

Leaf undulation of margin: Leaf undulation of margin as used herein is in accordance with the explanation of UPOV TG/245/1 Form, which recognizes three different levels: weak, medium, and strong.

Leaf width: Leaf width as used herein is in accordance with the explanation of UPOV TG/245/1 Form, which recognizes three different levels: narrow, medium, and broad.

Leaf width of primary lobes: Leaf width of primary lobes as used herein is in accordance with the explanation of UPOV TG/245/1 Form, which recognizes three different levels: narrow, medium, and broad.

Locus. Locus refers to the position or location of a gene on a chromosome.

Maturity date. Maturity refers to the stage when the plants are of full size or optimum weight, in marketable form or shape to be of commercial or economic value.

Plant height at flower stage. Plant height at flowering stage as used herein is in accordance with the explanation of UPOV TG/245/1 Form, which recognizes three different heights: short, medium, and long.

Plant Parts. As used herein, "plant parts" or "parts thereof" "is meant to refer to any part of the plant, including leaves, stems, and plant cells, and includes but is not limited to, regenerable cells which may include plant calli, plant clumps, plant protoplast, plant cells, plant cell tissue cultures, embryos, protoplasts, meristematic cells, callus, pollen, leaves, ovules, anthers, cotyledons, hypocotyl, pistils, roots, root tips, fruit, flowers, seeds, shoot, petiole, or stems.

Progeny. As used herein "progeny" is the descendants of one or more of the parental lines and includes an F1 plant produced from the cross of two arugula plants, such as where at least one plant includes 'CN SROC 2520'. Progeny further includes, but is not limited to, subsequent $F_2$, F3, F4, F5, F6, F7, F8, F9, and F10 generational crosses with the recurrent parental line or siblings.

Reference plant. As used herein "reference plant" is a known and available arugula cultivar that is uniform and stable, often the reference plant is a publicly available variety which can be used for comparison purposes to a different arugula variety including nucleic acid comparisons.

Timing of flowering: Time of flowering as used herein is in accordance with the explanation of UPOV TG/245/1 Form, which recognizes four different levels: early, medium, late, and very late.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

RHS. RHS refers to The Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering where essentially all of the desired morphological and physiological characteristics of a line are recovered in addition to the single gene transferred into the line via the backcrossing technique or via genetic engineering.

Sport, Spontaneous Mutation, Natural Mutation. As used herein, "sport" or "spontaneous mutation" or "natural mutation" refers to a mutation which has arisen spontaneously and has not been induced. These mutations may be selected from the initial variety and cultivated to produce an essentially derived variety. Sports, spontaneous mutations, and natural mutations may occur in an individual plant or on a plant part of the initial variety plant.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. In addition, the term "about" refers to a number that differs from the given number by less than 10%. In other embodiments, the term "about" indicates that the number differs from the given number by less than 9%, 8%, 7%, 6%, 5%, 4%, 3%, 2%, or 1%.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed.

Overview of the Variety 'CN SROC 2520'

'CN SROC 2520' is an arugula variety with dark green colored leaves, with small first true leaf that has a hint of lobes present, presents narrow to medium width of primary lobes, exhibits strong to very strong secondary lobbing, has an almost horizontal with round/smooth end angle of primary lobbing, and exhibits bolting/flowering medium to late.

Arugula variety 'CN SROC 2520' is the result of numerous generations of plant selections chosen for its ability to form good serration, darker green leaf color, and presence of lobes in first true leaf. 'CN SROC 2520' is the result of using variety 'CN SROC 2505', also known as 'Uber' (not patented) as the starting material beginning in 2013. Unlike the new variety 'CN SROC 2520', parent variety 'CN SROC 2505' has big unserrated to very little serration in first true leaf. Plants of variety 'CN SROC 2505' were grown in a controlled environment and allowed to pollinate. Thus, both parents of the new variety are 'CN SROC 2505'. 'CN SROC 2520' has been evaluated in numerous countries to determine how it grows and its characteristics in multiple climates/environments. This includes testing in Norway beginning in 2020; Denmark, Italy, Spain, and UK beginning in 2021; and Ireland beginning in 2022. Through these evaluations, it was determined that the seed performs in a true-to-type manner in these countries/climates/environments. A summary of the timeline of the selection of 'CN SROC 2520' is shown in Table 1.

TABLE 1

| Year | Activity |
|---|---|
| 2013 | single plant selection, which was selfed |
| 2014 | single plant selection, which was selfed |
| 2015 | small cage production |
| 2016 | in house trial followed by trial seed production |
| 2018 | trial seeds production |
| 2020-2022 | environmental testing in various countries in Europe |
| 2021-2022 | Distinctness, uniformity, and stability testing in The Netherlands |

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'CN SROC 2520'.

As of the date of filing there has been no sale, offer for sale, or public availability of the variety 'CN SROC 2520' in the United States or any else in the world.

Objective Description of the Variety 'CN SROC 2520'

Arugula variety 'CN SROC 2520' has the following morphologic and other characteristics:

Leaf:

Attitude: Semi-erect

Length: Medium

Width: Medium

Division: Strong

Width of primary lobes: Narrow to Medium

Secondary lobing: Strong to Very Strong

Color of blade: Green

Intensity of color: Dark
Undulation of margin: Very Weak
Hairiness: Very Weak

Plant:
Time of Flowering when 50% of Plant have at least One Open Flower:
Medium to Late
Height at flowering stage: Medium to Long Flower:
Color of petals: Light Yellow
Anthocyanin coloration of veins: Strong Growth Condition:
Time of flowering when 50% of plant have at least one open flower: Medium to late Comparisons to Other Arugula Varieties Table 2 below compares a characteristic of arugula variety 'CN SROC 2520' with the arugula variety 'Uber' (not patented), 'Oakley' (not patented), and 'Sky Rocket' (not patented). Column 1 lists the characteristic, column 2 shows the characteristic for arugula variety 'CN SROC 2520', column 3 shows the characteristic for arugula variety 'Uber', column 4 shows the characteristic for arugula variety 'Oakley', and column 5 shows the characteristic for arugula variety 'Sky Rocket'

TABLE 2

| Characteristic | 'CN SROC 2520' | 'Uber' | 'Oakley' | 'Sky Rocket' |
|---|---|---|---|---|
| Leaf color | Dark Green | Medium Green | Light Green | Light Green |
| Size of first true leaf | Smaller with presence of hint of lobes | Bigger with no hint of lobes | — | — |
| Leaf: width of primary lobes | Narrow to medium | Medium | — | — |
| Secondary lobbing (expressed after passing babyleaf stage) | Strong to very strong | Strong | Absent | — |
| Angle of primary lobbing | Almost horizontal with round/smooth end | — | Slightly upright angle with pointed end | — |
| Bolting/Flowering | Medium to late | Late | — | Late |

Gene Conversions

When the term "arugula plant" is used in the context of the present invention, this also includes any gene conversions of that variety. The term "gene converted plant" as used herein refers to those arugula plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental arugula plant which contributes the gene for the desired characteristic is termed the "nonrecurrent" or "donor parent." This terminology refers to the fact that the nonrecurrent parent is used one time in the backcross protocol and therefore does not recur. The parental arugula plant to which the gene or genes from the nonrecurrent parent are transferred is known as the recurrent parent as it is used for several rounds in the backcrossing protocol (see, e.g., Fehr (1993)). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until an arugula plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus.

In an embodiment, the invention relates to an arugula plant that has essentially all the morphological and physiological characteristics of 'CN SROC 2520' and has acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Tissue Culture

Further reproduction of the variety can occur by tissue culture and regeneration. Tissue culture of various tissues of arugula and regeneration of plants therefrom is well known. For example, Banjac et al., Horticulturae (2023), 9, 533. Thus, another aspect of this invention is to provide cells which upon growth and differentiation produce arugula plants having the physiological and morphological characteristics of variety 'CN SROC 2520'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art.

Additional Breeding Methods

The invention is also directed to methods for producing an arugula plant by crossing a first parent arugula plant with a second parent arugula plant where the first or second parent arugula plant is an arugula plant of variety 'CN SROC 2520'. Further, both first and second parent arugula plants can come from arugula variety 'CN SROC 2520'. Thus, any such methods using arugula variety 'CN SROC 2520', are part of the invention: selfing, backcrosses, hybrid production, crosses to populations, and the like. All plants produced using arugula variety 'CN SROC 2520' as at least one parent are within the scope of this invention, including those developed from varieties derived from arugula variety 'CN SROC 2520', also referred herein as "CN SROC 2520'-derived". Advantageously, this arugula variety could be used in crosses with other, different, arugula plants to produce the first generation (F1) arugula hybrid seeds and plants with superior characteristics. The variety of the invention can also be used for transformation where exogenous genes are introduced and expressed by the variety of the invention. Genetic variants created either through traditional breeding methods using arugula variety 'CN SROC 2520' or through transformation of variety 'CN SROC 2520' by any of a number of protocols known to those of skill in the art are intended to be within the scope of this invention.

The following describes breeding methods that may be used with arugula variety 'CN SROC 2520' in the development of further arugula plants. One such embodiment is a method for developing variety 'CN SROC 2520' progeny arugula plants in a arugula plant breeding program, by: obtaining the arugula plant, or a part thereof, of variety 'CN SROC 2520' utilizing said plant or plant part as a source of breeding material, and selecting a arugula variety 'CN SROC 2520' progeny plant with molecular markers in common with variety 'CN SROC 2520' and/or with morphological and/or physiological characteristics selected from the characteristics listed in the section entitled "Objective description of the variety 'CN SROC 2520'". Breeding steps that may be used in the arugula plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of arugula variety 'CN SROC 2520' progeny arugula plants, by crossing variety 'CN SROC 2520' with another arugula plant, thereby producing a population of arugula plants, which, on average, derive 50% of their alleles from arugula variety 'CN SROC 2520'. A plant of this population may be selected and repeatedly selfed or sibbed with an arugula variety resulting from these successive filial generations. One embodiment of this invention is the arugula variety produced by this method and that has obtained at least 50% of its alleles from arugula variety 'CN SROC 2520'. One of ordinary skill in the art of plant breeding would know how to evaluate the traits of two plant varieties to determine if there is no significant difference between the two traits expressed by those varieties. Thus the invention includes arugula variety 'CN SROC 2520' progeny arugula plants containing a combination of at least two variety 'CN SROC 2520' traits selected from those listed in the section entitled "Objective description of the variety 'CN SROC 2520', or the variety 'CN SROC 2520' combination of traits listed in the Summary of the Invention, so that said progeny arugula plant is not significantly different for said traits than arugula variety 'CN SROC 2520' as determined at the 5% significance level when grown in the same environmental conditions. Using techniques described herein, molecular markers may be used to identify said progeny plant as an arugula variety 'CN SROC 2520' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of arugula variety 'CN SROC 2520' may also be characterized through their filial relationship with arugula variety 'CN SROC 2520', as for example, being within a certain number of breeding crosses of arugula variety 'CN SROC 2520'. A breeding cross is a cross made to introduce new genetics into the progeny, and is distinguished from a cross, such as a self or a sib cross, made to select among existing genetic alleles. The lower the number of breeding crosses in the pedigree, the closer the relationship between arugula variety 'CN SROC 2520' and its progeny. For example, progeny produced by the methods described herein may be within 1, 2, 3, 4, or 5 breeding crosses of arugula variety 'CN SROC 2520'.

Gene Editing

Just as useful traits that may be introduced by backcrossing, useful traits may be introduced directly into the plant of 'CN SROC 2520', by genetic transformation techniques; and, such plants of 'CN SROC 2520' that have additional genetic information introduced into the genome or that express additional traits by having the DNA coding there for introduced into the genome via transformation techniques, are within the ambit of the invention, as well as uses of such plants, and the making of such plants.

Gene editing can be done through a variety of techniques including zinc finger nucleases and CRISPR/Cas9 technology. See e.g., Saunders & Joung, NATURE BIOTECHNOLOGY, 32, 347-355, 2014. CRISPR is a type of targeted genome editing system that stands for Clustered Regularly Interspaced Short Palindromic Repeats. This system and CRISPR-associated (Cas) genes naturally enable organisms, such as select bacteria and archaea, to respond to and eliminate invading genetic material. See e.g., Ishino, et al., J. BACTERIOL. 169, 5429-5433 (1987). CRISPR/Cas9 technology is used for direct gene editing, in vivo and in vitro. Many plants have already been modified using the CRISPR system. See e.g., International Publication No. WO2014/068346; Martinelli, et al., *Proposal of a Genome Editing System for Genetic Resistance to Tomato Spotted Wilt Virus* 2014 AMERICAN JOURNAL OF APPLIED SCIENCES; Noman, et al., *CRISPR-Cas9: Tool for Qualitative and Quantitative Plant Genome Editing*, November 2016 FRONTIERS IN PLANT SCIENCE Vol. 7; and Zhang et al., *Exploiting the CRISPR/Cas9 System for Targeted Genome Mutagenesis in Petunia* February 2016 SCIENCE REPORTS Volume 6.

Additional information about CRISPR/Cas9 system technology including crRNA-guided surveillance complex systems for gene editing may be found in the following documents: U.S. Application Publication No. 2010/0076057; U.S. Application Publication No. 2014/0179006; U.S. Pat. No. 10,000,772; U.S. Application Publication No. 2014/0294773; Sorek et al., ANNU. REV. BIOCHEM. 82:273-266, 2013; and Wang, S. et al., PLANT CELL REP (2015) 34:1473-

1476. Therefore, it is another embodiment to use gene editing, including the CRISPR/Cas9 system, on 'CN SROC 2520' to modify traits, such as hardiness and resistances or tolerances to pests, herbicides, diseases, and viruses.

Genetic transformation may therefore be used to insert a selected transgene into the plant of 'CN SROC 2520', or may, alternatively, be used for the preparation of transgenes which may be introduced by backcrossing. Methods for the transformation of plants, are well known to those of skill in the art.

Vectors used for the transformation of arugula cells are not limited so long as the vector may express an inserted DNA in the cells. For example, vectors which may comprise promoters for constitutive gene expression in arugula cells (e.g., cauliflower mosaic virus 35S promoter) and promoters inducible by exogenous stimuli may be used. Examples of suitable vectors include pBI binary vector. The "arugula cell" into which the vector is to be introduced includes various forms of arugula cells, such as cultured cell suspensions, protoplasts, leaf sections, and callus. A vector may be introduced into arugula cells by known methods, such as the polyethylene glycol method, polycation method, electroporation, Agrobacterium-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

One efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target arugula cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of arugula variety 'CN SROC 2520'.

Agrobacterium-mediated transfer is another widely applicable system for introducing gene loci into plant cells. An advantage of the technique is that DNA may be introduced into whole plant tissues, thereby bypassing the need for regeneration of an intact plant from a protoplast. Agrobacterium transformation vectors are capable of replication in *E. coli* as well as Agrobacterium, allowing for convenient manipulations. Moreover, advances in vectors for Agrobacterium-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, Agrobacterium containing both armed and disarmed Ti genes may be used for transformation. In those plant strains where Agrobacterium-mediated transformation is efficient, it is the method of choice because of the facile and defined nature of the gene locus transfer. The use of Agrobacterium-mediated plant integrating vectors to introduce DNA into plant cells, including lettuce plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for arugula plant gene expression include, but are not limited to, the cauliflower mosaic virus (CaMV) P-35S promoter, a tandemly duplicated version of the CaMV 35S promoter, the enhanced 35S promoter (P-e35 S), the nopaline synthase promoter, the octopine synthase promoter, the figwort mosaic virus (P-FMV) promoter (see, e.g., U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from lettuce (psaD, psaF, psaE, PC, FNR, atpC, atpD, cab, rbcS), the CAB-1 promoter from spinach (see, e.g., U.S. Pat. No. 7,663,027), the promoter from maize prolamin seed storage protein (see, e.g., U.S. Pat. No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wunl, or (5) chemicals such as methyl jasmonate, salicylic acid, or Safener. It may also be advantageous to employ organ-specific promoters.

Exemplary nucleic acids which may be introduced to the arugula variety 'CN SROC 2520', for example, DNA sequences or genes from another species, or even genes or sequences which originate with or are present in arugula species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of 'CN SROC 2520'. Non-limiting examples of particular genes and corresponding phenotypes one may choose to introduce into a arugula plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (a ribozyme) engineered to cleave a desired endogenous mRNA product. Thus, any gene which produces a protein or mRNA which expresses a phenotype or morphology change of interest is useful for the practice of the present invention (see, e.g. U.S. Pat. No. 7,576,262).

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems.

The invention provides a method of producing an arugula seed which may comprise crossing a male parent arugula plant with a female parent arugula plant and harvesting the resultant arugula seed, wherein said male parent arugula plant and/or said female parent arugula plant is the arugula plant of grown from a seed of 'CN SROC 2520', a sample of seed of said variety having been deposited under NCIMB Accession Number NCIMB 44773. The invention includes an arugula seed produced by this method and an arugula plant produced by growing said seed.

Also, the invention relates to methods for producing a seed of a 'CN SROC 2520'-derived arugula plant which may comprise (a) crossing a plant of 'CN SROC 2520', representative seed of which having been deposited under NCIMB Accession Number NCIMB 44773, with a second arugula plant, and (b) whereby seed of a CN SROC 2520'-derived arugula plant forms. Such a method may further comprise (c) crossing a plant grown from 'CN SROC 2520'-derived arugula seed with itself or with a second arugula plant to yield additional 'CN SROC 2520'-derived arugula seed, (d) growing the additional 'CN SROC 2520'-derived arugula seed of step (c) to yield additional 'CN SROC 2520'-derived arugula plants, and (e) repeating the crossing and growing of steps (c) and (d) for an additional 2, 3, 4, 5, 6, 7, 8, 9, or 10 generations or for an additional 3-10 generations to generate further 'CN SROC 2520'-derived arugula plants, and (f) whereby seed of a 'CN SROC 2520'-derived arugula plant forms.

The invention further relates to the above-described methods that may further comprise selecting at steps b), d), and e), a 'CN SROC 2520'-derived arugula plant, exhibiting a combination of traits including darker green leaf color and presence of lobes in first true leaf.

Food Product

The invention relates to a method of producing arugula leaves as a food product which may comprise sowing the seed of arugula variety 'CN SROC 2520' or of a 'CN SROC 2520'-derived variety, and growing the seed into a harvestable arugula plant and harvesting the leaves of said plant.

The invention further includes a method for producing arugula leaves as a fresh vegetable which may comprise packaging leaves of a plant of arugula variety 'CN SROC 2520' or of a 'CN SROC 2520'-derived variety, and a method for producing arugula leaves as a processed food which may comprise processing leaves of a plant of arugula variety CN SROC 2520' or of a 'CN SROC 2520'-derived variety.

Arugula leaves may be sold in packaged form, including without limitation as pre-packaged arugula salad or as arugula heads. Many forms of packaging are known in the art, such as packaging film, and packages from such packaging film, including such packaging containing leafy produce, and methods for making and using such packaging film and packages, which are suitable for use with the arugula leaves of the invention (see, e.g., U.S. Pat. No. 5,523,136). Thus, the invention comprehends the use of and methods for making and using the leaves of the arugula plant of the invention, as well as leaves of arugula plants derived from the invention. The invention further relates to a container which may comprise one or more plants of the invention, or one or more arugula plants derived from a plant of the invention, for harvest of leaves from the plant. More generally, the invention includes one or more plants of 'CN SROC 2520' or one or more plants derived from arugula plant 'CN SROC 2520', wherein the plant is in a ready-to-harvest condition, including with the consumer picking his own, and further including a container which may comprise one or more of these plants.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

The invention claimed is:

1. An arugula seed designated as 'CN SROC 2520', wherein a representative sample of said arugula seed having been deposited with NCIMB Accession number NCIMB 44773.

2. A plant produced by growing the arugula seed of claim 1.

3. A plant, or a plant part thereof, having all the physiological and morphological characteristics of the plant of claim 2.

4. A part of the plant of claim 3, wherein said part is a leaf, a shoot, a stem, and/or a portion thereof.

5. A part of the plant of claim 3, wherein said part is a leaf.

6. A part of the plant of claim 3, wherein said part is a microspore, pollen, an ovary, an ovule, an embryo sac or an egg cell, a cutting, a root, a stem, a cell or a protoplast.

7. A tissue culture of regenerable cells or protoplasts from the plant or plant part of claim 3.

8. A method of making arugula seeds, the method comprising crossing a male parent arugula plant with a female parent arugula plant and harvesting the resultant arugula seeds therefrom, wherein said male parent arugula plant or said female parent arugula plant is the plant of claim 2.

9. An F1 arugula seed produced by the method of claim 8.

10. An F1 arugula plant produced by growing the seed of claim 9.

11. A method of making arugula seeds, the method comprising crossing a male parent arugula plant with a female parent arugula plant and harvesting the resultant arugula seeds therefrom, wherein said male parent arugula plant and said female parent arugula plant is the plant of claim 2.

12. An arugula plant produced by growing the seed of claim 11.

13. A method for producing a seed of a 'CN SROC 2520'-derived arugula plant, the method comprising:

(a) crossing a plant of arugula variety 'CN SROC 2520', wherein a representative seed of which having been deposited with NCIMB Accession number NCIMB 44773, with a second arugula plant, and (b) whereby seed of a 'CN SROC 2520'-derived arugula plant forms.

14. The method of claim 13, further comprising:

(c) crossing a plant grown from the seed of (b) with itself or with a second arugula plant to yield additional 'CN SROC 2520'-derived arugula seed, (d) growing the additional 'CN SROC 2520'-derived arugula seed of step (c) to yield additional 'CN SROC 2520'-derived arugula plants, (e) repeating the crossing and growing of steps (c) and (d) for an additional 3-10 generations to generate further 'CN SROC 2520'-derived arugula plants, and (f) whereby seed of a 'CN SROC 2520'-derived arugula plant forms.

15. A method of generating an arugula variety, the method comprising:

(a) crossing a plant of arugula variety 'CN SROC 2520', wherein a representative seed of which having been deposited with NCIMB Accession number NCIMB 44773, with a plant of a second arugula variety that comprises at least one distinct trait from arugula variety 'CN SROC 2520' to produce progeny seed;

(b) harvesting and planting the progeny seed to produce at least one progeny plant of a subsequent generation;

(c) crossing the progeny plant with either a plant of arugula variety 'CN SROC 2520' or a plant of the second arugula variety to produce backcross progeny seed;

(d) harvesting and planting the backcross progeny seed to produce a backcross progeny plant; and (e) repeating steps (c) and (d) for one or more additional generations to produce an arugula plant of variety comprising all of the physiological and morphological characteristics of a plant of arugula variety 'CN SROC 2520' and optionally comprising at least one distinct trait of the second arugula variety, when grown in the same environmental conditions.

16. A method of producing a plant of arugula variety 'CN SROC 2520' comprising at least one new trait, the method comprising introducing a mutation or transgene conferring the at least one new trait into a plant of arugula variety 'CN SROC 2520', wherein a sample of seed of said variety has been deposited with NCIMB Accession number NCIMB 44773.

17. A method for producing arugula leaves as food product, the method comprising sowing the seed of claim 1 and growing the seed into a harvestable arugula plant and harvesting the leaves of said plant.

18. A method for producing arugula leaves as a fresh vegetable, the method comprising packaging leaves of a plant of claim 2.

19. A method for producing arugula leaves as a processed food, the method comprising processing leaves of a plant of claim 2.

20. A container comprising one or more arugula plants of claim 2 or plant part(s) thereof.

21. A method of determining the genotype of a plant of arugula variety 'CN SROC 2520', wherein a representative seed of which has been deposited with NCIMB Accession number NCIMB 44773, or a first generation progeny thereof, the method comprising obtaining a sample of nucleic acids from said plant and comparing said nucleic acids to a sample of nucleic acids obtained from a reference plant, and detecting a polymorphism between the two nucleic acid samples.

* * * * *